US009683949B2

(12) United States Patent
Lee et al.

(10) Patent No.: US 9,683,949 B2
(45) Date of Patent: Jun. 20, 2017

(54) NON-DESTRUCTIVE QUANTITATIVE WELD QUALITY MEASUREMENT USING RADIOGRAPHIC IMAGING

(71) Applicant: Toyota Motor Engineering & Manufacturing North America, Inc., Erlanger, KY (US)

(72) Inventors: Gary Lee, Cambridge (CA); Jason David Hind, Cambridge (CA); William Brad Cheeseman, Cambridge (CA)

(73) Assignee: TOYOTA MOTOR ENGINEERING & MANUFACTURING NORTH AMERICA, INC., Erlanger, KY (US)

( * ) Notice: Subject to any disclaimer, the term of this patent is extended or adjusted under 35 U.S.C. 154(b) by 190 days.

(21) Appl. No.: 14/610,571

(22) Filed: Jan. 30, 2015

(65) Prior Publication Data
US 2016/0223477 A1 Aug. 4, 2016

(51) Int. Cl.
*G01N 23/18* (2006.01)
*G01N 23/04* (2006.01)
(52) U.S. Cl.
CPC ............ *G01N 23/18* (2013.01); *G01N 23/04* (2013.01); *G01N 2223/629* (2013.01)
(58) Field of Classification Search
CPC ...... G01N 23/04; G01N 23/08; G01N 23/083; G01N 19/08; G01N 2223/6291; B23K 31/12; B23K 31/125; B23K 26/03
See application file for complete search history.

(56) References Cited

U.S. PATENT DOCUMENTS

| 3,466,418 A | 9/1969 | Webb | |
|---|---|---|---|
| 4,694,479 A * | 9/1987 | Bacskai | G01N 23/18 378/58 |
| 6,204,469 B1 * | 3/2001 | Fields, Jr. | B23K 26/032 219/121.6 |

(Continued)

FOREIGN PATENT DOCUMENTS

FR   2923606 A1 *   5/2009   ........... B23K 11/252

OTHER PUBLICATIONS

Hse, "Information for the Procurement and Conduct of NDT", Apr. 2008, 24 pages.

(Continued)

*Primary Examiner* — David E Smith
(74) *Attorney, Agent, or Firm* — Christopher G. Darrow; Darrow Mustafa PC

(57) ABSTRACT

A method for quantitatively assessing a quality of a weld joint includes positioning an electromagnetic radiation source adjacent the weld joint. The electromagnetic radiation source may be aligned to direct a beam of electromagnetic radiation onto the weld joint. A detector for capturing the electromagnetic radiation emitted from the electromagnetic radiation source may be positioned adjacent the weld joint along a side opposite the electromagnetic radiation source, such that the weld joint is positioned between the electromagnetic radiation source and the detector. A radiographic image of the weld joint may be obtained by directing the beam of electromagnetic radiation toward the weld joint and onto the detector. A weld joint quality rating may be determined for the weld joint based at least in part on the radiographic image.

20 Claims, 3 Drawing Sheets

(56) References Cited

U.S. PATENT DOCUMENTS

| | | | | |
|---|---|---|---|---|
| 6,414,261 B1* | 7/2002 | Maetschke | ........... | B23K 11/252 |
| | | | | 219/109 |
| 2004/0245315 A1* | 12/2004 | Maev | ................... | G01N 29/262 |
| | | | | 228/8 |
| 2014/0153693 A1* | 6/2014 | Nishimoto | ............. | G01N 23/04 |
| | | | | 378/58 |
| 2014/0348415 A1* | 11/2014 | Bhattad | ................ | B23K 31/125 |
| | | | | 382/152 |
| 2016/0125764 A1* | 5/2016 | Becker | ................... | G09B 19/24 |
| | | | | 434/234 |

OTHER PUBLICATIONS

Kocak, "Defect Assessment of Spot Welds by NDI", Thesis, The Middle East Technical University, Sep. 2003, 242 pages.

* cited by examiner

NON-DESTRUCTIVE QUANTITATIVE WELD QUALITY MEASUREMENT USING RADIOGRAPHIC IMAGING

BACKGROUND

Various destructive and non-destructive inspection methods and techniques have been developed for examining weld joints in welded assemblies. The methods include various non-destructive inspection techniques utilizing, for example, eddy-current, ultrasonic and radiographic technologies. These non-destructive inspection methods allow the welded assemblies to be used after the inspection process is completed. Other weld inspection techniques tend to be destructive in nature and may render the welded assembly unsuitable for use after the inspection process is completed. For example, inspection techniques involving sectioning and subsequent microscopic examination of the weld are destructive in nature and typically do not permit use of the welded assembly after inspection. Further, destructive weld inspection techniques are capable of only providing a reasonable indication of a probable rather than actual quality of the welds being produced. Thus, non-destructive inspection techniques tend to be more useful for determining a quality of the welds that will actually be placed in service.

SUMMARY

Disclosed is an apparatus and method for inspecting a weld joint using non-destructive radiographic imaging. The disclosed inspection process is particularly applicable to spot welds. The process involves obtaining a digital radiographic image of a weld joint. The radiographic image may alternatively be captured on film and converted to a digital image for analysis. A spot weld may appear on the radiographic image as a dark spot surrounded by a brighter corona. The dark spot indicates a location of a weld nugget and the brighter corona corresponds to a heat affected zone caused by the welding process. A light intensity level of the dark spot corresponding to the weld nugget indicates the quality of the weld joint. Generally speaking, a lower the light intensity level (i.e., darker the spot) the better the weld quality. A quantitative weld joint quality rating may be determined based on data obtained from the radiographic image. The weld joint quality rating represents the quality of the weld joint and may be used to evaluate whether the quality of the weld joint is sufficient or further inspection of the weld joint may be warranted.

BRIEF DESCRIPTION OF THE DRAWINGS

The various features, advantages and other uses of the present apparatus will become more apparent by referring to the following detailed description and drawings, in which.

DETAILED DESCRIPTION

Figure 1:
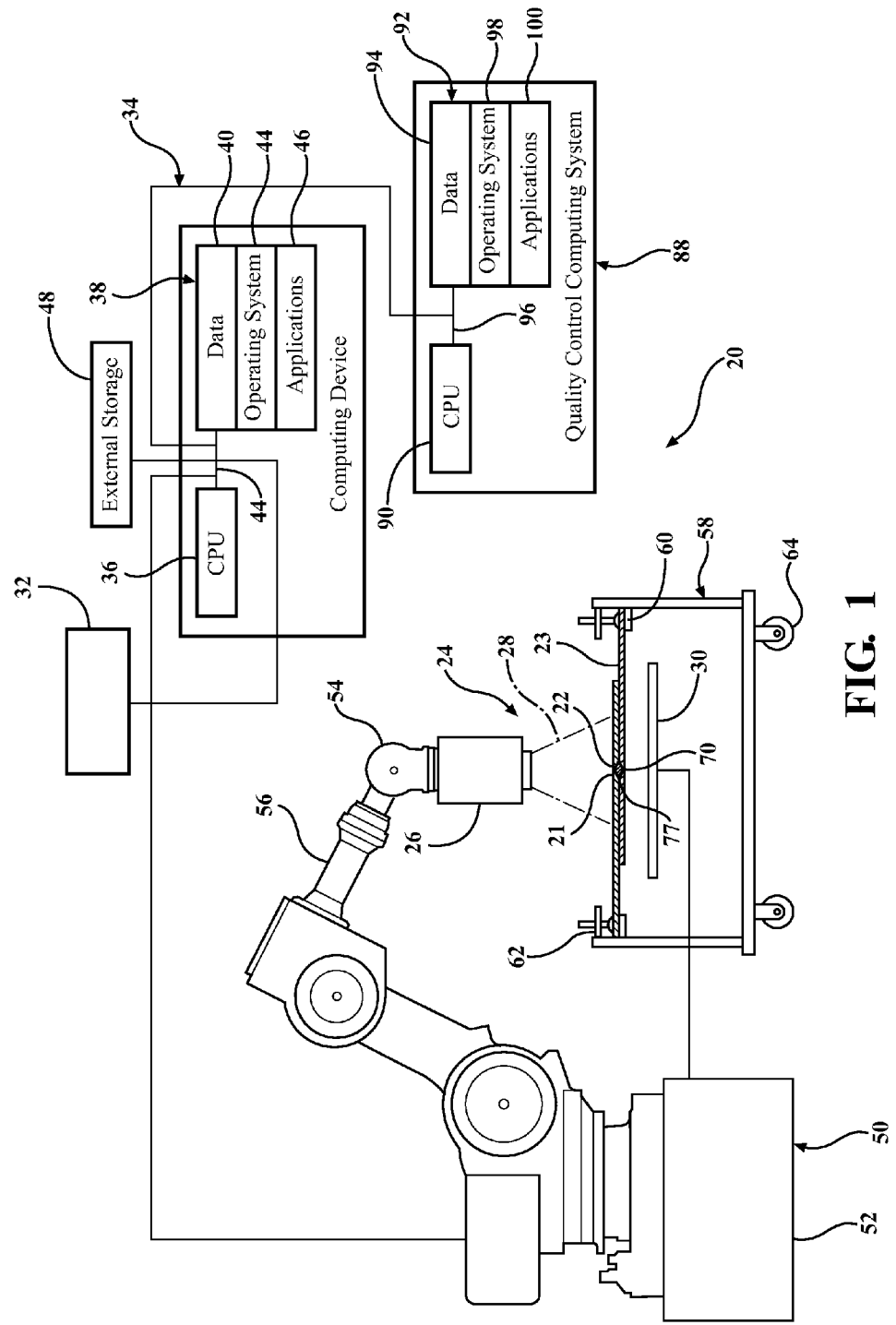
FIG. 1 is a schematic illustration of an exemplary radiographic inspection system for performing non-destructive testing of a weld joint.

Disclosed is an apparatus and method for inspecting a weld joint using non-destructive radiographic imaging. The disclosed inspection process may be particularly applicable to spot welds. The process involves obtaining a digital radiographic image of a weld joint. The radiographic image may alternatively be captured on film and converted to a digital image for analysis. A spot weld may appear on the radiographic image as a dark spot surrounded by a brighter corona. The dark spot indicates a location of a weld nugget and the brighter corona corresponds to a heat affected zone caused by the welding process. A light intensity level of the dark spot corresponding to the weld nugget indicates the quality of the weld joint. Generally speaking, a lower the light intensity level (i.e., darker the spot) the better the weld quality. A quantitative weld joint quality rating may be determined based on data obtained from the radiographic image. The weld joint quality rating represents the quality of the weld joint and may be used to evaluate whether the quality of the weld joint is sufficient or further inspection of the weld joint may be warranted.

Referring now to the discussion that follows and also to the drawings, illustrative approaches to the disclosed systems and methods are described in detail. Although the drawings represent some possible approaches, the drawings are not necessarily to scale and certain features may be exaggerated, removed, or partially sectioned to better illustrate and explain the present invention. Further, the descriptions set forth herein are not intended to be exhaustive or otherwise limit or restrict the claims to the precise forms and configurations shown in the drawings and disclosed in the following detailed description.

FIG. 1 illustrates an exemplary radiographic inspection system 20 for performing non-destructive examination of a weld joint 21, and in particular, as spot weld, formed in a workpiece 23 to determine its quality. The radiographic inspection system 20 may employ a radiographic imaging system 24 for obtaining radiographic images of the weld joint 21. Various imaging technologies may be employed to obtain the radiographic images of the weld joint 21, including but not limited to, digital radiography (also known as radioscopy) and film radiography. The radiographic imaging system 24 may include an electromagnetic radiation source 26 operable to generate an electromagnetic radiation beam 28 and a detector 30 for capturing the electromagnetic radiation energy emitted from the radiation source 26. The electromagnetic radiation source 26 and the detector 30 are generally arranged on opposite sides of the weld joint 21 that is being inspected. The electromagnetic radiation source 26 may be positioned such that the electromagnetic radiation beam 28 is directed onto the weld joint 21. Electromagnetic radiation passing through the workpiece 23 and weld joint 21 may be captured by detector 30.

The electromagnetic radiation beam 28 emitted from radiation source 26 may operate at a range of frequencies, such X-rays and gamma-rays. Thick materials may require use of higher energy electromagnetic radiation than thin materials to obtain a satisfactory radiographic image. X-rays typically have lower energy than gamma-rays and may be better suited for examining thin materials, whereas higher energy gamma-rays may be better suited for examining thicker materials. In practice, the operating parameters of the electromagnetic radiation used to generate a radiographic image may be tailored to accommodate the physical and material characteristics of particular weld joint being inspected.

With continued reference to FIG. 1, the detector 30 may have any of various configurations. For example, the detector 30 may be configured as a digital detector or a film based detector. Configurations employing a film based detector may require additional image processing equipment for converting a film based radiographic image to a digital image suitable for further electronic processing. A digital detector may be configured to include a fluorescent screen or an array of solid state sensors. The digital detector may also employ re-usable flexible phosphor plates to capture images. After being exposed to electromagnet radiation emitted from electromagnetic radiation source 26, the exposed plates may be processed through a laser scanner to produce an image that may be delivered to a monitor 32 for viewing. The resulting digital image, whether originating from a film based detector or a digital detector, may be electronically stored for future retrieval and analysis. These are only of few examples of the types of detector technologies that may be employed with detector 30. Other methods and/or technologies capable of producing high quality digital radiographic images may also be employed.

Continuing to refer FIG. 1, the radiographic imaging system 24 may include an image processor 34, which may be operably connected to the electromagnetic radiation source 26 and the detector 30. The image processor 34 may be any type of handheld, desktop, or other form of single computing device, or may be composed of multiple computing devices. The processing unit in the image processor 34 may be a conventional central processing unit (CPU) 36 or any other type of device, or multiple devices, capable of manipulating or processing data and information. A memory 38 of the image processor 34 may be a random access memory device (RAM) or any other suitable type of storage device. Memory 38 may include data 40 that may be accessed by CPU 36 using a bus 42.

Memory 38 may also include an operating system 44 and installed applications 46, including programs that enable the CPU 36 to control operation of the radiographic imaging system 24, as well as analyze and process the data and information collected by the detector 30. The image processor 34 may also include secondary, additional, or external storage 48, for example, a memory card, flash drive, or any other form of computer readable medium. The installed applications 46 may be stored in whole or in part in the external storage 48 and loaded into the memory 38 as needed for processing.

To facilitate positioning of the electromagnetic radiation source 26, particularly in manufacturing environments employing automated production systems, the radiation source may be attached to a robot 50. The robot 50 may have any of a variety of configurations depending on the requirements of a particular application. The robot 50 may include multiple servo mechanisms for controlling movement of the robot 50. The servo mechanisms are capable of generating forces that cause the robot 50 to perform a desired movement. For example, the servos mechanisms may cause rotation of the robot 50 about its base 52, as well as rotation of a wrist 54 of the robot 50 relative to an arm 56 of the robot 50. The CPU 36 of the image processor 34 may be in communication with the robot servos mechanisms to control movement of the robot 50.

With continued reference to FIG. 1, the radiographic inspection system 20 may include a fixture 58 for supporting the workpiece 23 relative to the electromagnetic radiation source 26 and the detector 30. The fixture 58 may include various features for securely supporting the workpiece 23. For example, the fixture may include various pins 60 engageable with the workpiece 23 and clamping devices 62 for securing the workpiece 23 to the fixture 58. The fixture 58 may be stationary or moveable. For example, the fixture may include rollers 64 to facilitate positioning the fixture 58 and the workpiece 23 relative to the radiographic imaging system 24. Configuring the fixture 58 to be moveable allows the fixtures 58 to be preloaded with a workpiece 23 prior to being moved into position relative to the radiographic imaging system 24.

The radiographic imaging inspection system 20 may be employed in connection with an automated production system, such as an assembly line. The assembly line may consist of multiple workstations that include various tooling and equipment used to produce the workpiece 23, and may include forming, cutting, welding and assembly equipment. The radiographic inspection system 20 may be one of multiple work stations arranged along the assembly line. The fixture 58 may be used to transport the workpiece 23 between workstations of the assembly line. The radiographic inspection system 20 may be an integral part of the assembly line and configured to automatically inspect the weld joint 21.

Employing the robot 50 to position the electromagnetic radiation source 26 relative to the weld joint 21 and the fixture 58 for transporting the workpiece 23 to and from the radiographic inspection system 20 facilitates automatic operation of the radiographic inspection system 20. For example, the fixture 58 may be used to transport and position the workpiece 23 within the radiographic inspection system 20. With the workpiece 23 positioned within the radiographic inspection system 20, the image processor 34 may operate robot 50 to position the electromagnetic radiation source 26 relative to the weld joint 21. The radiographic imaging system 24 may then be activated to obtain a radiographic image of the weld joint 21. When the inspection process is completed, the fixture 58 may be moved to transport the workpiece 23 out of the radiographic inspection system 20.

Figure 2:
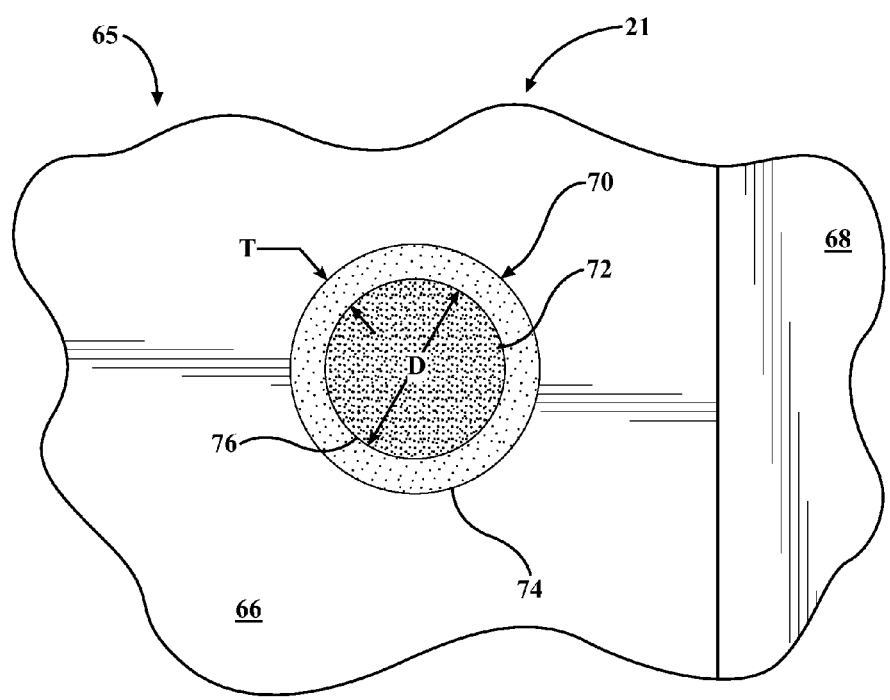
FIG. 2 is a schematic illustration of a radiographic image of an exemplary spot weld.

FIG. 2 schematically illustrates an example of a radiographic image 65 of the weld joint 21 formed in workpiece 23 that may be captured using the radiographic imaging system 24. The weld joint 21 may be formed by joining a first sheet metal panel 66 to a second sheet metal panel 68. In this particular example, a spot weld 70 is used to join the sheet metal panels, but other welding techniques may also be employed.

With continued reference to FIG. 2, the spot weld 70 may appear in the radiographic image 65 as a generally circular-shaped spot having a dark center region 72 surrounded by a corona 74. The corona 74 may appear brighter in the radiographic image 65 than the center region 68. The center region 68 generally coincides with a location of the weld nugget 22 of the spot weld 70 (see FIG. 1). An outer boundary 76 of the center region generally corresponds to an outer boundary 77 of the weld nugget 22. The weld nugget 22 is formed during the welding process and results from local melting of the first and second sheet metal panels 66 and 68. The melted material solidifies to form the weld nugget 22. The size of the weld nugget 22 generally corresponds to the size of the center region 72 in the radiographic image 65. Generally speaking, the larger the center region 72 the larger the weld nugget 22.

Although the center region 72 is illustrated as having a substantially circular shape, in practice the center region 72 may also have any other geometric shape. The actual size and shape of the center region 72, and correspondingly, the size of the weld nugget 22, may be dependent on various factors, including but not limited to, the shape of electrodes used to produce the spot weld 70, the material composition of the sheet metal panels 66 and 68, the presence of debris on a surface of the sheet metal panels 66 and 68, and a thickness of the sheet metal panels 66 and 68, as well as other factors. The center region 72 may have an average diameter "D".

The corona 74 encircling the weld nugget 22 (i.e., center region 72) generally corresponds to a heat affected zone caused by the welding process. The corona 74 typically extends outward from the center region 72, and may have a radial thickness "T". The corona 74 may appear to be brighter than the center region 72 in the radiographic image 65. The size and shape of the of the corona 74 may vary depending on various factors, including but not limited to, the shape of the electrodes used to produce the spot weld 70, the material composition of the sheet metal panels 66 and 68, the presence of debris on the surface of the sheet metal panels 66 and 68, and a thickness of the sheet metal panels 66 and 68, as well as other factors. It is possible that a spot weld may not produce a corona 74 that is detectable in the radiographic image 65.

With continued reference to FIG. 2, a quality of the weld joint 21 may be assessed and quantified based on information collected from the radiographic image 65. The radiographic image 65 may reveal several detectable weld quality indicators that individually and/or collectively may be used to qualitatively assess the quality of the weld joint 21. The weld quality indicators may include, for example, the average diameter D of the center region 72, the radial thickness T of the corona 74, and an average light intensity level of the center region 72. In particular, it has been determined that an average light intensity level of the center region 72 is a reasonably accurate indicator of the quality of the spot weld 70. For example, a low light intensity level (i.e., dark center region 72) generally corresponds to a better quality weld joint. Conversely, a high light intensity level (i.e., bright center region 72) may indicate a poorer quality weld joint.

A weld joint quality rating may be determined for the spot weld 70 based at least in part on the average light intensity level of the center region 72. The weld quality rating may be determined directly from information obtained from the radiographic image 65 when formatted as a digital image. Additional processing may be required to determine the average light intensity level of the center region 72 when the radiographic image is formatted as a film based image.

Figure 4:
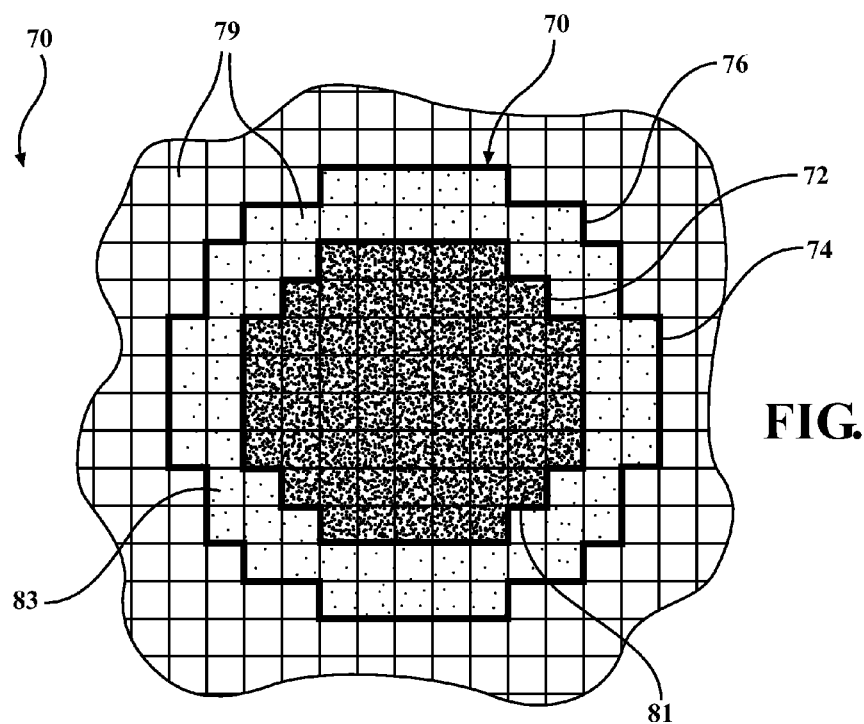
FIG. 4 is a close-up view of the radiographic image illustrated in FIG. 2.

When formatted as a digital black-and-white image, the radiographic image 65 may be composed of shades of gray, varying from black at the weakest light intensity level to white at the strongest light intensity level. A magnified view of an exemplary digital image 78 of spot weld 70 is schematically illustrated in FIG. 4. The digital image 78 may be made up of a plurality of adjoining generally square-shaped pixels 79. A light intensity level of each individual pixel 79 may vary to produce the radiographic image of the spot weld 70. In the exemplary digital image 78, the darker shaded pixels 81 correspond to the center region 72 of the spot weld 65, and the lighter shaded pixels 83 correspond to the corona 74. In the example image illustrated in FIG. 4, the pixels 82 corresponding to the center region 72 are all shown to have substantially the same light intensity level. Similarly, the pixels 83 corresponding to the corona 74 are all shown to have substantially the same light intensity level. In practice, however, the individual pixel corresponding to the center region 72 and the corona 74 will likely have differing light intensity levels.

The weld joint quality rating may be computed for the spot weld 70 by separately determining a light intensity level for each of the individual pixels 81 that together form the center region 72. The light intensities of the pixels 81 forming the center region 72 may then be numerically averaged to determine the weld quality rating of the spot weld 70.

To assess whether a particular weld joint has sufficient quality based on its determined weld joint quality rating, the weld joint quality rating may be compared against a database of verified weld joint quality ratings for similarly configured weld joints for which the quality of the weld joint has been previously confirmed. The database of verified weld quality ratings may be stored in memory 38 of image processor 34, or external storage 48. Verifying a quality of a weld joint may include destructively testing the weld joint to confirm its actual quality.

Figure 3:
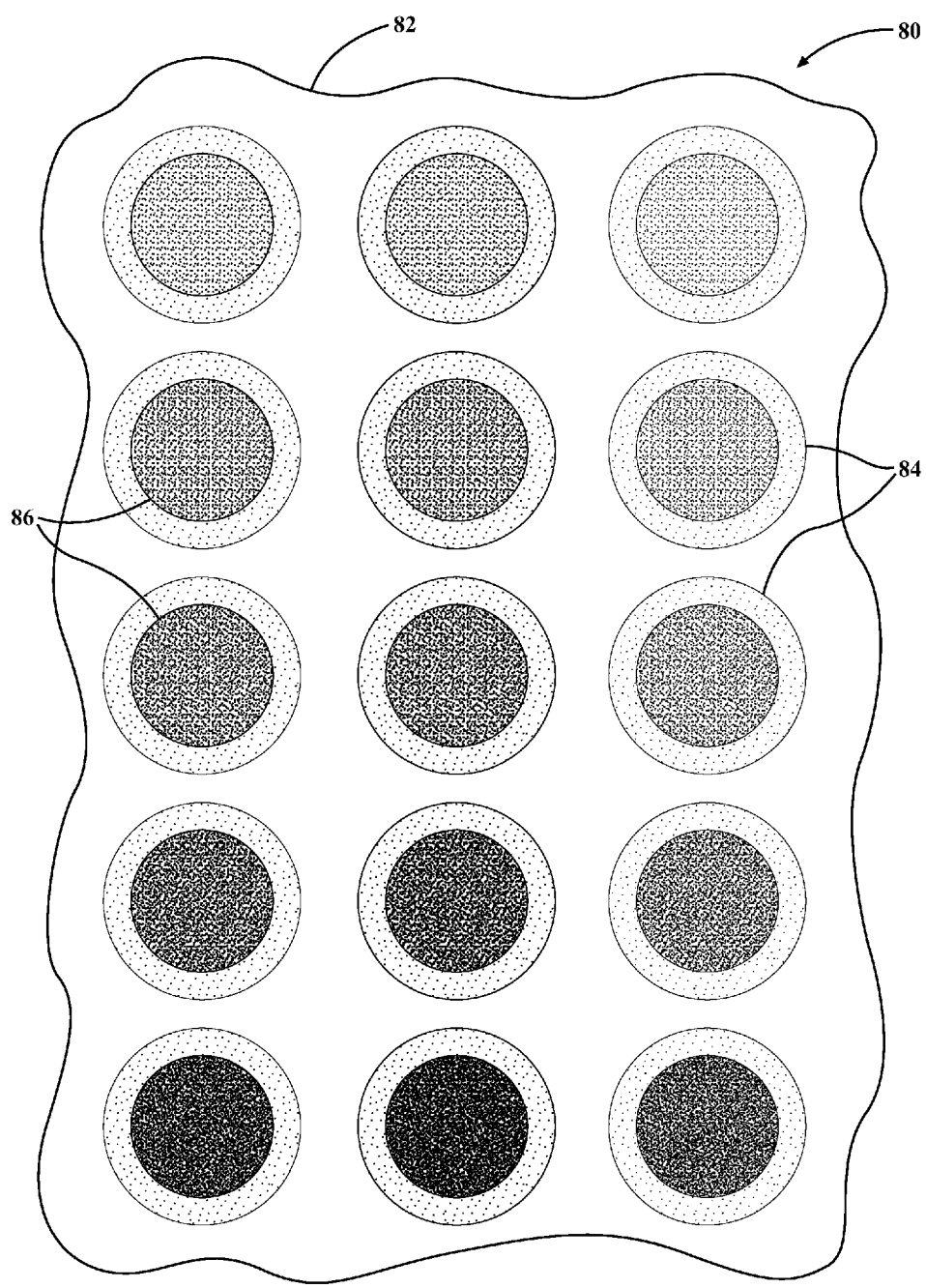
FIG. 3 is a schematic illustration of a radiographic image of sample test panel including multiple spot welds of varying weld quality.

With reference to FIG. 3, verified weld joint quality ratings for populating the verified weld joint quality rating database residing in memory 38 of image processor 34 may be generated, for example, by producing a test panel having multiple spot welds of differing quality. A radiographic image of the test panel may be captured using the radiographic imaging system 24. An example of a radiographic image 80 of a test panel 82 is illustrated in FIG. 3. The exemplary test panel 82 includes multiple test spot welds 84. Each test spot weld 84 may have a different weld joint quality rating, as evidenced by a change in light intensity level of a center region 86 of the spot welds 84. A verified spot weld quality rating may be determined for each of the test spot welds 84 of the test panel 82. The verified spot weld quality rating may be determined in the manner previously described for determining the spot weld quality rating of spot weld 70. Each test spot weld 84 may be physically inspected to confirm the quality of each test spot weld 84, thereby correlating the physically determined weld quality rating with the verified weld joint quality rating.

To confirm that spot weld 70 is of sufficient quality, the computed weld joint quality rating for spot weld 70 may be compared against the verified weld joint quality ratings residing in memory 38 of image processor 34. If the computed weld joint quality rating for spot weld 70 is less than a predetermined value, the spot weld 70 may be rejected or flagged for further inspection. The additional inspection may include physically inspecting the spot weld 70 or performing a destructive test procedure on the spot weld. The inspection procedure may also include performing a chisel test on the spot weld 70.

Digital radiographic images of spot welds, and their associated weld joint quality ratings, may be stored electronically in a historical weld quality database that may reside in memory 38 of image processor 34. Alternatively, the radiographic images and associated weld joint quality ratings may be stored in a historical weld quality database that may be separate from image processor 34, such as external storage 48. The stored information may be monitored to detect changes in weld quality that may occur, for example, in a manufacturing production line. In addition to helping ensure production of quality parts, the ability to efficiently monitor weld quality levels may provide other benefits, such as detecting problems with production equipment that may adversely affect weld quality and require equipment maintenance to correct. For example, a detected decrease in weld quality may indicate that electrodes on a spot welder are worn and need replacing.

The historical weld quality database residing in memory 38 of image processor 34 may be configured to electronically store historical weld joint quality ratings related to a particular weld joint. The weld joint quality ratings may relate to a particular spot weld on a workpiece, such as spot 70 on workpiece 23. The stored weld joint quality ratings may be monitored to detect changes in the quality of welds being produced. If a significant change in the weld joint quality rating is detected, a physical inspection of the weld joint and/or welding equipment may be initiated to determine the source of the problem and plan corrective action.

With reference to FIG. 1, image processor 34 may be in communication with one or more secondary computing systems, such as a quality control system 88. The quality control system 88 may be configured to further process the data and information collected and/or generated by the radiographic inspection system 20. The quality control system 88 may be configured for long term electronic storage of electronic weld data and information, including weld joint quality ratings, received from image processor 34.

The quality control system 88 may be similarly configured as image processor 34. For example, quality control system 88 may be any type of handheld, desktop, or other form of single computing device, or may be composed of multiple computing devices. The processing unit in the quality control system 88 may be a conventional central processing unit (CPU) 90 or any other type of device, or multiple devices, capable of manipulating or processing data and information. A memory 92 of the quality control system 88 may be a random access memory device (RAM) or any other suitable type of storage device. The memory 92 may include data 94 that may be accessed by the CPU 90 using a bus 96.

Memory 94 may also include an operating system 98 and installed applications 100, including programs that analyze and process the data and information received from image processor 34.

The quality control system 88 may be configured to perform any of the processes performed by image processor 34, including conducting historical analysis of the weld joint quality ratings stored in the historical weld quality database residing in memory 38 of image processor 34. The historical weld quality database may also be configured to reside in memory 94 of quality control system 88.

It is intended that the scope of the present methods and apparatuses be defined by the following claims. However, it must be understood that the disclosed systems and methods may be practiced otherwise than is specifically explained and illustrated without departing from its spirit or scope. It should be understood by those skilled in the art that various alternatives to the configurations described herein may be employed in practicing the claims without departing from the spirit and scope as defined in the following claims. The scope of the disclosed systems and methods should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc., should be read to recite one or more of the indicated elements unless a claim recites an explicit limitation to the contrary. It is intended that the following claims define the scope of the device and that the method and apparatus within the scope of these claims and their equivalents be covered thereby. In sum, it should be understood that the device is capable of modification and variation and is limited only by the following claims.

What is claimed is:

1. A method for quantitatively assessing a weld joint, the method comprising:
    positioning a radiation source adjacent a weld joint of a workpiece, the radiation source aligned to direct a radiation beam onto the weld joint;
    positioning a detector adjacent the weld joint along a side of the workpiece opposite the radiation source, the weld joint positioned between the radiation source and the detector;
    obtaining a radiographic image of the weld joint by directing the radiation beam toward the weld joint and onto the detector;
    determining a weld joint quality rating based at least in part on the radiographic image; and
    initiating a physical inspection of the weld joint when the weld joint quality rating is determined to be less than a predetermined value.

2. The method of claim 1 further comprising evaluating a weld quality of the weld joint by electronically comparing the radiographic image of the weld joint to a radiographic image of at least one other weld joint having a previously determined weld joint quality rating.

3. The method of claim 1, wherein determining the weld joint quality rating comprises determining a light intensity level of the weld joint based at least in part on the radiographic image.

4. The method of claim 1, wherein the weld joint is a spot weld and determining the weld joint quality rating comprises:
    determining a boundary of a weld nugget region based at least in part on the radiographic image; and
    determining a light intensity of the weld nugget region based at least in part on the radiographic image.

5. The method of claim 4, wherein determining the weld joint quality rating comprises determining an average diameter of the weld nugget region based at least in part on the radiographic image.

6. The method of claim 5, wherein determining the weld joint quality rating includes determining a radial thickness of a weld corona extending outward from the weld nugget region based at least in part on the radiographic image.

7. The method of claim 4, wherein the weld nugget region is defined in the radiographic image by a plurality of pixels and determining the weld joint quality rating comprises determining a light intensity of each of the plurality of pixels.

8. The method of claim 7, wherein determining the weld joint quality rating comprises determining an average light intensity of the plurality of pixels defining the weld nugget region.

9. The method of claim 1, wherein the radiation beam is at least one of an x-ray and a gamma-ray.

10. The method of claim 1, wherein the radiographic image is a digital image.

11. The method of claim 1, wherein the physical inspection of the weld joint includes performing a destructive test procedure.

12. The method of claim 11, wherein performing the destructive test procedure includes performing a chisel test procedure.

13. A method for monitoring a quality of weld joints in a manufacturing environment, the method comprising:

obtaining a first digital radiographic image of a first weld joint by directing a radiation beam from a radiation source toward the first weld joint and onto a detector;

computing a first weld joint quality rating based at least in part on an average light intensity level of a center region on the first digital radiographic image;

obtaining a second digital radiographic image of a second weld joint by directing the radiation beam from the radiation source toward the second weld joint and onto the detector;

computing a second weld joint quality rating based at least in part on an average light intensity level of a center region on the second digital radiographic image; and monitoring a change in weld joint quality by comparing the first weld joint quality rating to the second weld joint quality rating and physically inspecting at least one of the first and second weld joints when a difference between the first weld joint quality rating and the second weld joint quality rating is greater than a predetermined value.

14. The method of claim 13, wherein computing the first and second weld joint quality ratings comprises:

determining a boundary of a first weld nugget region based at least in part on the first digital radiographic image;

determining a boundary of a second weld nugget region based at least in part on the second digital radiographic image;

determining a light intensity of the first weld nugget region based at least in part on the first digital radiographic image; and determining a light intensity of the second weld nugget region based at least in part on the second digital radiographic image.

15. The method of claim 14 further comprising initiating a physical inspection of the second weld joint when a difference in light intensity between the first weld nugget region and the second weld nugget region is greater than a predetermined amount.

16. The method of claim 13, wherein computing the first and second weld joint quality ratings comprises determining an average diameter of the first weld nugget region based at least in part on the first digital radiographic image and determining an average diameter of the second weld nugget region based at least in part on the second digital radiographic image.

17. The method of claim 16, wherein computing the first and second weld joint quality ratings comprises:

determining a radial thickness of a first weld corona extending outward from the first weld nugget region based at least in part on the first digital radiographic image; and determining a radial thickness of a second weld corona extending outward from the second weld nugget region based at least in part on the second digital radiographic image.

18. The method of claim 13, wherein the first and second weld nugget regions are defined in the respective first and second digital radiographic images by a plurality of pixels, and computing the first and second weld joint quality ratings comprises determining a light intensity of each of the plurality of pixels for each of the first and second weld nugget regions.

19. The method of claim 18, wherein computing the first and second weld joint quality ratings comprises determining an average light intensity of the plurality of pixels of the first and second weld nuggets.

20. The method of claim 13, wherein the radiation beam is at least one of an x-ray and a gamma-ray.

* * * * *